(12) United States Patent
Kerr et al.

(10) Patent No.: US 10,941,064 B2
(45) Date of Patent: Mar. 9, 2021

(54) INOCULANT FOR WATER TREATMENT DEVICE

(71) Applicant: BIOFILM SOLUTIONS, INC., New Paltz, NY (US)

(72) Inventors: Donald Kerr, New Paltz, NY (US); Roy Morrison, Leonia, NJ (US); Lisa Albanese, Central Valley, NY (US)

(*) Notice: Subject to any disclaimer, the term of this patent is extended or adjusted under 35 U.S.C. 154(b) by 672 days.

(21) Appl. No.: 14/682,934

(22) Filed: Apr. 9, 2015

(65) Prior Publication Data

US 2015/0291461 A1    Oct. 15, 2015

Related U.S. Application Data

(60) Provisional application No. 61/979,238, filed on Apr. 14, 2014, provisional application No. 61/988,672, filed on May 5, 2014.

(51) Int. Cl.
| | |
|---|---|
| C02F 3/34 | (2006.01) |
| C02F 3/02 | (2006.01) |
| C02F 3/28 | (2006.01) |
| C12N 1/20 | (2006.01) |
| C02F 3/00 | (2006.01) |
| C02F 3/12 | (2006.01) |
| C02F 3/04 | (2006.01) |

(52) U.S. Cl.
CPC .............. *C02F 3/341* (2013.01); *C02F 3/006* (2013.01); *C02F 3/02* (2013.01); *C02F 3/28* (2013.01); *C02F 3/348* (2013.01); *C12N 1/20* (2013.01); *C02F 3/04* (2013.01); *C02F 3/1257* (2013.01); *C02F 2209/001* (2013.01); *C02F 2209/08* (2013.01); *C02F 2209/10* (2013.01); *C02F 2209/16* (2013.01); *C02F 2209/36* (2013.01); *C02F 2209/40* (2013.01); *C02F 2303/04* (2013.01); *C02F 2305/06* (2013.01); *Y02W 10/10* (2015.05)

(58) Field of Classification Search
CPC .. C02F 3/341; C02F 3/006; C02F 3/02; C02F 3/28; C02F 3/348; C02F 3/04; C02F 3/1257; C02F 3/34; C02F 2209/001; C02F 2209/08; C02F 2209/10; C02F 2209/16; C02F 2209/36; C02F 2209/40
USPC ........................................... 210/610
See application file for complete search history.

(56) References Cited

U.S. PATENT DOCUMENTS

2010/0065509 A1* 3/2010 Kerr .................. C02F 1/001
                                                                  210/747.3

* cited by examiner

*Primary Examiner* — Robert Clemente
*Assistant Examiner* — Akash K Varma
(74) *Attorney, Agent, or Firm* — Brownstein Hyatt Farber Schreck, LLP

(57) ABSTRACT

The invention provides inoculants for the generation of a biologically active layer in a water treatment or purification device. In some embodiments, the invention provides inoculants for a biologically active zone in a wastewater treatment system or device, for example in municipal wastewater and sewage treatment. In other aspects, the invention provides inoculants for water purification, for example in municipal drinking water purification or in slow sand filtration. Inoculants of the invention increase the effectiveness of the above systems and devices in providing useable water.

19 Claims, No Drawings

INOCULANT FOR WATER TREATMENT DEVICE

RELATED APPLICATIONS

This application claims priority under 35 U.S.C. 119 (e) to U.S. Provisional Patent Application Ser. No. 61/979,238, entitled "INOCULANT FOR WATER TREATMENT DEVICE", filed Apr. 14, 2014, and U.S. Provisional Patent Application Ser. No. 61/988,672, entitled "INOCULANT FOR WATER TREATMENT DEVICE", filed May 5, 2014, the disclosures of which are hereby incorporated by reference in their entirety.

TECHNICAL FIELD

The invention generally relates to water treatment devices. More particularly, the invention relates to inoculants for water treatment and high capacity treatment of water supplies that service users of water treatment devices, for example in municipal drinking water and wastewater treatment facilities.

BACKGROUND OF THE INVENTION

Water treatment is essential to generate a usable and consistent water supply for various human uses, such as drinking, sewage, irrigation, and industrial processes. There is a need for improved water treatment devices and processes in both the developed and developing world, as the developing world lacks access to safe water supplies, and the developed world lacks water treatment capacity to provide useful water for human uses.

A lack of wastewater treatment capacity reduces the amount of useful water available to a municipality, resulting in increased water costs and restrictions and limitations on the use of treated wastewater. Treated wastewater is typically used as an alternative to the use of potable water for agricultural and industrial uses, though use as a source of drinking water is increasing due to improvements in large-scale wastewater treatment operations. At a minimum, wastewater or sewage must be treated to a level suitable for release into the surrounding environment.

Numerous methods and devices for wastewater treatment are used, generally incorporating one or more of physical, chemical, and biological processes. In a typical process, sewage or wastewater is pretreated to remove solids, then subjected to one or more additional chemical or biological processes to generate an environmentally-acceptable effluent. Often, the biological processes require the generation of a biologically active zone, which may be a biofilm or layer which contains organisms capable of processing water contaminants. Some of the systems using a biofilm include sequencing batch reactors, activated sludge systems, and rotating biological contactors. Each of these methods requires generation of the biofilm, often taking weeks or months before the effluent water is useful. Because the devices must sometimes be cleaned to restore water flow, they experience significant periods where water is not treated to a useable level, requiring backup systems for significant downtime.

The developing world also relies on municipal water treatment. Lack of safe water, including water borne diseases, is reported responsible for 80 percent of illnesses and deaths in the developing world. A significant amount of disease can be prevented, especially in developing countries, through better access to safe water supply, adequate water treatment facilities, and better hygiene practices. Comparison of statistics indicates some progress in rural water supply development in terms of the percentage of population supplied with water, but there is some regression in urban water supply mainly because of population drift from rural to urban areas. It is estimated that domestic water use in developing countries will raise six fold over the coming four decades, placing severe strain on surface and ground water supplies. Therefore, there is an increasing need to provide safe domestic water supplies, especially in developing and rural areas of the world.

The developing world heavily uses water treatment devices incorporating biological layers. Slow sand filtration is a method of producing potable water from a non-potable source, for example from untreated surface water. Slow sand filters are a preferred water treatment technique for the developing world because they are inexpensive and require no energy source. Additionally, some cities such as London use slow sand filters in the purification of household water, and many additional systems may benefit from their use, such as hydroponic systems.

Unlike other water treatment or purification techniques, slow sand filters do not rely on size exclusion or temperature elevation to eliminate water-borne pathogens. Instead, they rely on a complex biological layer or biofilm, often called a hypogeal layer or a Schmutzdecke, that forms on the surface of the sand. This layer consists of one or more of bacteria, fungi, protozoa, rotifera, aquatic insect larvae, algae, and larger aquatic organisms including bryzoa, snails, and Annelid worms. As water passes through the Schmutzdecke, particles of foreign matter are trapped in the mucilaginous matrix and organic matter is adsorbed and metabolized by organisms. Typically, at least 10-21 days are required to establish an effective Schmutzdecke in a new filter.

Once established, a well-managed slow sand filter can provide high quality potable water, however as the Schmutzdecke continues to grow into a thicker layer, water production is eventually reduced, and cleaning is required. One method employed to clean the filter is to scrape off the Schmutzdecke to expose a new layer of clean sand. This removes the ability of a filter to produce potable water for some time, as a new Schmutzdecke must form. Another method, often called wet harrowing, involves lowering the water level, stirring the Schmutzdecke, and then running off the suspended particles. While this method preserves more of the Schmutzdecke and allows potable water flow to be reestablished more quickly, it does not clean the filter as thoroughly and still requires significant amounts of time before water potability is regained.

The time required to establish a slow sand filter and the inefficiency of the cleaning techniques discussed above results in the need for a larger number of slow sand filters to provide a consistent source of potable water, as well as wasted non-potable water in areas where there is already limited access to water.

The invention is directed toward overcoming one or more of the problems discussed above.

SUMMARY OF THE INVENTION

The invention provides compositions and methods for generating a biologically active zone in a water treatment device. Water treatment devices using biologically active zones are used both in municipal water systems and in the developing world. Aspects of the invention are useful for increasing the effectiveness of said water filters.

In one aspect, an inoculant for the generation of a biologically active zone in a water treatment device is provided, where the inoculant comprises organisms preserved from a water treatment device. In some aspects, the water treatment device is a wastewater treatment device. In certain embodiments, the wastewater treatment devices are selected from one or more of a biological, aerobic, anaerobic, digestor, lagoon or reactor-based device. In other embodiments, the water treatment device is a drinking water treatment device. In some embodiments, the drinking water treatment device is a slow sand filter. In some aspects, the inoculant comprises organisms suspended in a nutrient solution. In certain embodiments, the organisms suspended in the nutrient solution are bacteria.

Other aspects of the invention include methods of generating an inoculant for water treatment by harvesting biologically active material from a water treatment device and preserving organisms from the harvested biologically active material. In some embodiments, the water treatment device is a wastewater treatment device. In certain embodiments, the wastewater treatment device is one or more of a biological, aerobic, anaerobic, digestor, lagoon, or reactor-based device. In other embodiments, the water treatment device is a drinking water treatment device. In some embodiments, the drinking water treatment device is a slow sand filter. In some aspects, the organisms are suspended in a nutrient solution. In additional aspects, the organisms suspended in the nutrient solution are bacteria.

Still other aspects of the invention include methods of rapidly generating a biologically active zone in a water treatment device in need thereof by placing an inoculant of organisms preserved from a first water treatment device into a second water treatment device and allowing water to flow through the inoculant. In some embodiments, the water treatment device is a wastewater treatment device. In certain embodiments, the wastewater treatment device is one or more of a biological, aerobic, anaerobic, digestor, lagoon or reactor-based device. In other embodiments, the water treatment device is a drinking water treatment device. In some embodiments, the drinking water treatment device is a slow sand filter. In certain embodiments, additional nutrients are provided to the organisms before being placed in to the water purifier.

Aspects of the invention also include methods of replacing a biologically active zone of a water treatment device in need thereof by removing biologically active material from the purifier to restore effective water flow, and applying an inoculant of organisms preserved from a water treatment device into the device in an amount that decreases the time before treated water is generated. In certain embodiments, the inoculant contains organisms having the regional characteristics of those found in the previously removed biologically active material.

Additional aspects of the invention include methods for increasing the production of treated water from a wastewater treatment device by removing biofilm material in a sufficient amount to restore the desired water flow, placing an inoculant comprising organisms preserved from a biofilm into the device, and allowing water to flow through the device, treating the water more quickly than if inoculant was not added.

Other aspects of the invention include methods of increasing the production of potable water from a slow sand filter by removing Schmutzdecke to restore water flow, placing an inoculant of organisms preserved from Schmutzdecke into the filter, and allowing water to flow through the filter, making the water potable more quickly than if the inoculant were not present. In certain embodiments, the method further comprises determining the potability of the filtered water. In other embodiments, the inoculant comprises organisms having the regional characteristics found in the removed Schmutzdecke. In yet other embodiments, additional nutrients are added with the inoculant or inflowing water. Other embodiments include keeping the influent water turbidity to equal or less than 10.00 NTU, and still further embodiments include keeping the effluent water turbudity to equal or less than 1.00 NTU.

Another aspect of the invention includes methods of rapidly supplying treated water to a community by providing a water source with a turbidity of 10.00 NTU or less, providing a portable water treatment device with an inoculant of organisms preserved from a water treatment device, flowing water from the water source through the inoculant to cause biological reactivation, and collecting the effluent water.

These and various other features and advantages of the invention will be apparent from a reading of the following description and a review of the appended claims.

DESCRIPTION

Aspects of the invention provide an inoculant for the generation of a biologically active zone in a water treatment device. Embodiments of the invention are particularly beneficial in drinking or wastewater treatment, particularly to municipal water treatment facilities, or to individuals or clustered communities that lack the capacity to receive improved water, for example in the developing world.

In aspects of the invention, an inoculant is provided to aid in the generation or regeneration of an effective biologically active zone in a water treatment device requiring said zone for the production of useful water. Water treatment devices include any devices that use and develop such a biologically active layer, and typically are those designed with a substrate suitable for the development of such a layer. Preferred water treatment devices are drinking water and waste treatment devices. In some embodiments, the device is a slow sand filter, for example those found in U.S. Patent Publication No. 2010/0065509, hereby incorporated by reference for all uses. In other embodiments, the device is a water treatment device used as part of a larger municipal water system, such as in wastewater treatment. In preferred embodiments, the wastewater treatment device is selected from one or more of a biological, aerobic, anaerobic, digestor, lagoon or reactor-based device.

In embodiments of the invention, the inoculant comprises organisms preserved from the biologically active zone of a water treatment device. In a preferred embodiment, the inoculant comprises organisms preserved from the biologically active zone of a wastewater treatment device. In another embodiment, the inoculant comprises organisms preserved from the biologically active zone of a drinking water treatment device. In specific embodiments, the inoculant comprises organisms preserved from the Schmutzdecke of a slow sand filtration device or biofilm from a wastewater treatment device.

Complex biologically active zones and biofilms are formed on various water treatment devices, and may comprise one or more of bacteria, fungi, protozoa, rotifera, aquatic insect larvae, algae, and larger aquatic organisms including bryzoa, snails, and Annelid worms. The composition of any particular biofilm varies based on the organisms found in the attachment substrate and the water source. As the biological layer develops, a gelatinous biofilm matrix forms and water flows through the matrix slowly, allowing the organisms to feed on and remove organisms that are harmful to the environment and human health. A properly functioning biofilm may achieve 90-99+ percent reductions in water-borne bacteria and viruses, and may provide virtually complete removal of *Giardia lamblia* cysts and *Cryptosporidium* oocysts.

As the biofilm grows, its ability to remove unwanted material and organisms from the water increases, however the output of water eventually decreases to an unusable level, at which point the layer must be removed to generate the desired flow. Typically, the water is drained from the treatment device, the biofilm is removed, and water flow is reestablished. Another method involves lowering the water level, stirring or agitating the biofilm, and then running off the water, removing part of the layer.

Either of these methods requires reestablishment of the biologically active layer before effluent water is usable. This typically takes a week or more, and in municipal sewage treatment may occur over months. Additionally, the process requires that the filter be run, resulting in wasted water and the need for several devices in any given treatment operation. This places a relatively high burden on all operators of devices incorporating a biologically active layer. In the developing world, limited financial resources constrain the number of filters that may be established, and limited water resources may result in a lack of immediately available water for other uses, such as agriculture. In large-scale municipal filtration operations, a larger number of filters may be required, requiring additional space and a significant reduction in the cost effectiveness of the operation.

The inoculant provided in embodiments of the invention speeds the production of a biologically active zone, improving the effectiveness of water treatment devices and operations.

In some embodiments, the inoculant is generated from biologically active material removed from a water treatment device. In one embodiment, removed material is run through a filter to eliminate larger debris, leaving any desired microorganisms. These microorganisms may be preserved for future use by any conventional means, e.g. by one or more of suspension in a nutrient-rich solution, freeze-drying or dehydration, or cryogenic storage. In some embodiments, the inoculant is a suspension in nutrient-rich solution, and may be of any suitable size, for example less than about 1 mL, about 1 mL, about 10 mL, about 50 mL, about 100 mL, about 500 mL, about 1 L, about 2 L, about 5 L, about 10 L, about 50 L, about 100 L, or more than about 100 L.

In other embodiments, the biologically active material is removed as a substantially complete layer, i.e. containing part of the substrate. In typical slow sand filter embodiments, the removed layer typically has a thickness of approximately six inches. In municipal water treatment devices, the layer may be substantially thicker. Biologically active material removed as a layer may be preserved by any of the conventional means discussed above. More preferably, the layer is preserved by freeze-drying or dehydration. It is expected that freeze-drying or dehydration will allow a substantial number of organisms to survive, and has the additional benefit of allowing substrate material to be preserved. Additionally, freeze-drying or dehydration provides an inoculant with a long shelf life and low shipping weight, allowing efficient shipping and storage, leading to reductions in the price of implementing water treatment devices, especially the developing world.

In a preferred embodiment, biologically active material is removed in a substantially intact layer or as a piece that comprises a substantially intact layer, e.g. containing substantially all of the substrate and microorganisms found from the top to the bottom of the layer. In some embodiments, sand or other substrate material is also included. In slow sand filter embodiments, the layer typically has a thickness of about six inches, not including any additional sand or other substrate material. It is anticipated that including additional substrate material will allow water purification to be reestablished more quickly in the filter. In a preferred embodiment, the substantially intact biologically active layer is preserved by freeze-drying or dehydration, optionally including any additional substrate material taken from the filter when the layer was removed.

In some embodiments, the inoculant comprises bacteria or other microorganisms derived from the biologically active zone of a water treatment device or from a water source and cultured or grown to a suitable population by conventional means, such as agitation in a nutrient-rich environment, i.e. a laboratory flask or container containing a growth medium, or growth on a nutrient-rich medium, i.e. agar plates containing a growth medium. In other embodiments, the inoculant comprises bacteria or other microorganisms not directly derived from the biologically active zone of a water treatment device but nonetheless suitable for use in water treatment.

In embodiments of the invention, the inoculant comprises nutrients that aid in the selective growth of beneficial microorganisms in the inoculant, e.g., growth agents or food sources. In some embodiments, the nutrients are provided to facilitate establishment of the biologically active zone and/or to minimize the time required to establish a functional biologically active zone. Exemplary nutrients include sugars and carbohydrates, vitamins and minerals, and pH modifiers.

In some embodiments, the inoculant comprises one or more selective antimicrobial agents. Antimicrobial agents are typically selected for their ability to eliminate or prevent the growth of undesirable organisms found in the environment of the treatment device, allowing desirable organisms of the inoculant to preferentially multiply in the inoculant and the treatment device. The antimicrobial agents may be selected from antibacterial, antifungal, antiviral, antiparasitic, or other agents, and may include pharmaceutical compounds, such as antibiotics, and non-pharmaceutical compounds, such as silver or a bleach.

Embodiments of the invention also provide kits comprising an inoculant comprising organisms preserved from a water treatment device. In some embodiments, the kit may additionally contain one or more of nutrients, a water treatment device, instructions for the set up and use of said device, tools for setting up the device, and devices for testing the usefulness or potability of the effluent water. In some embodiments, the kit is for the establishment of a slow sand filtration device, and includes the filtration device, inoculant, tools, and instructions for establishing the device. In a preferred embodiment, the kit includes the filtration device, an inoculant comprising a preserved (i.e. freeze-dried or dehydrated) layer of Schmutzdecke, optional nutrients, optional tools and instructions, and optional devices for testing the potability of the effluent water.

In other embodiments, the kit is for the cleaning or replacement of a biologically active zone in an established filtration device, and includes an inoculant, instructions, and optionally tools for the removal of biologically active material and insertion of the inoculant. In a preferred embodiment, the kit comprises a preserved (i.e. freeze-dried or dehydrated) layer of the biologically active zone of a water treatment device, optional nutrients, and optional tools and instructions for the replacement of biologically active material in a water treatment device. The kit may additionally comprise devices for testing the potability or usefulness of effluent water.

Embodiments of the invention additionally provide methods for generating an inoculant for water treatment. In a preferred embodiment, an inoculant is generated from the existing biological material of the water filter to be cleaned. In other embodiments, the inoculant may be generated from biologically active material of another treatment device and selected for its ability to treat water having a certain profile or composition of microorganisms, for example the water of a specific region or source.

Because biozones for water treatment are typically generated in-place from influent "dirty" water sources and contain multiple types of organisms ranging from bacteria and viruses to Annelid worms and larger organisms, the biozones formed by different water sources is likely to vary. Thus, an inoculant generated from one source or region may have limited effectiveness in regions having a substantially different microorganism profile.

In some methods of the invention, biologically active material is harvested from a water treatment device and organisms are preserved from the material to generate an inoculant for water treatment. In a preferred embodiment, the organisms are predominantly bacteria harvested from the water treatment device, cultured in a nutrient-rich environment, and preserved for storage and later use in seeding a device in need thereof. The preserved organisms may be kept in continuous culture or otherwise made suitable for long-term storage and regeneration.

Additionally, the invention includes methods for rapidly generating a biologically active layer in a water treatment device in need thereof, comprising placing an inoculant containing preserved organisms into a water treatment device and allowing water to flow through the device, causing the biologically active layer to generate. In a preferred embodiment, nutrients are provided to the preserved organisms before placing them into the device. In other embodiments, nutrients are provided before, during, or after the organisms are placed into the device.

Embodiments of the invention also provide methods for replacing a biologically active zone of a water treatment device in need thereof, comprising removing biologically active material in an amount sufficient to restore effective water flow, and applying an inoculant comprising organisms preserved from a water treatment device into the device in an amount effective to decrease the length of time before treated water is generated. In certain embodiments, the inoculant comprises organisms having the regional characteristics of those found in the removed biologically active material, allowing for rapid regeneration of an effective biozone.

Aspects of the invention provide methods for increasing the production of treated water from a wastewater treatment device, comprising removing biofilm material from a wastewater treatment device in an amount sufficient to restore desired water flow, placing an inoculant comprising organisms preserved from a biofilm into the wastewater treatment device, and allowing water to flow through the wastewater treatment device, producing treated water more quickly than if the inoculant were not added.

Other aspects of the invention provide methods for increasing the production of potable water from a slow sand water filter, comprising removing Schmutzdecke from a slow sand water filter in an amount sufficient to restore the desired water flow, placing an inoculant comprising organisms preserved from Schmutzdecke into the slow sand water filter, and allowing water to flow through the slow sand water filter, wherein the water is made potable more quickly than if inoculant is not added. The method may further comprise determining the potability of the filtered water, for example by conventional testing methods and devices. Exemplary methods include determination of one or more of the particulate load, any reduction in the particulate load, bacterial speciation, organic load, nitrogen loads, reduction in the nitrogen load, and coliform load and any reduction in coliform load.

In embodiments of the above method, the inoculant contains organisms having the regional characteristics of those found in the removed Schmutzdecke. In yet other embodiments, additional nutrients are provided during one or more stages of performing the method, for example when adding the inoculant, and/or when restoring water flow over the filter.

In embodiments of the above method, the water is made potable much more quickly than if the inoculant is not added. In conventional methods of cleaning a slow sand filter, the effluent water is typically not potable until 1-3 weeks have passed, and often is not potable until 2-6 weeks have passed, as the biological layer must attain sufficient density and diversity before it entraps and processes bacteria and other organisms detrimental to human health. In this method, the inoculant immediately increases the abundance of beneficial bacteria and other microorganisms, reducing the amount of time required before potable water is produced. For example, methods of the invention may produce potable water in two weeks or less, more preferably one week or less, and most preferably within 12, 24, 48, 72, 96, 120, or 144 hours.

In preferred embodiments of the above method, the influent water turbidity is less than or equal to 10.00 NTU, as determined by use of a calibrated nephelometer. In other embodiments, the effluent water has a turbidity of equal to or less than 1.00 NTU.

The invention also provides methods for rapidly supplying treated water to a community, comprising providing a water source having a turbidity of 10.00 NTU or less, providing a portable water treatment device comprising an inoculant containing organisms preserved from a water treatment device, flowing water from the water source through the inoculant so as to cause biological reactivation, and collecting the effluent water. This method allows faster generation of treated or potable water and better serves the needs of both municipalities and the developing world. In a preferred embodiment, a kit containing a slow sand filter and inoculant is provided to a community in need of water filtration.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

Definitions

"Inoculant" as used herein refers to a composition of matter containing beneficial materials, including but not limited to bacteria and small organisms, growth mediums, nutrients, and structural materials, useful for the development of organisms and substrates for the purposes of the invention.

"Biological" as used herein refers to materials which comprise organisms, living and/or dead, such as microfauna, microflora, macrofauna, and macroflora, and may contain viral, bacterial, plant, and animal cells or organisms, as well as their waste.

"Biologically active" as used herein refers to the property of a composition where the composition contains living organisms functioning in aspects of their normal lifecycle, i.e. nutrient consumption, respiration, and reproduction.

"Biologically active zone," "biozone," and similar uses refer to a specific area or region comprising biological and biologically active materials as defined above. Such area is typically located on a substrate to facilitate the attachment of flora and fauna, however it may also be any region having the activity of the above referenced materials.

"Water treatment device" refers to a device or composition capable of generating effluent water more suitable for use or consumption than the inflowing water source. Exemplary devices include those for wastewater treatment and potable water purification, and may include processes or structures comprising biological, chemical, and mechanical treatments. In some cases, the device is a system of components, and may reference an entire facility or municipal water treatment system.

"Wastewater treatment device" refers to any water treatment device used or constructed for recycling previously used water into a more suitable or useable form, including but not limited to water suitable for industrial, agricultural, municipal, or personal use.

"Drinking water treatment device" refers more specifically to any water treatment device used for improving the quality of water so as to increase the suitability of the water for personal consumption.

EXAMPLES

The following examples are provided for illustrative purposes only and are not intended to limit the scope of the invention.

Example 1

Creation of Inoculant from Slow Sand Filter

A P3 BioSand Bag Filter (BioSand Bag Filter, LLC, New Paltz, N.Y.) is established in a sterile laboratory using a non-sterile inflowing water source and sand as the filtration substrate. The water flow is controlled, allowing a biologically active layer to form over a period of weeks. The effluent water may be tested at this time to determine the potability of the water and effectiveness of the filter.

Biologically active material is removed from the filter after reaching appropriate maturity, as determined by relevant measures, i.e. thickness or filtration characteristics. Removed material is freeze-dried or dehydrated by conventional methods to form the inoculant, and is stored for later use. The remaining sand is left intact in the filter for future regeneration of the biologically active layer.

Example 2

Evaluation of Biologically Active Material From Multiple Water Inflows

Two separate P3 BioSand Bag Filters are established in a sterile laboratory using two biologically non-identical, non-sterile inflowing water sources and sand as the filtration substrate. For each bag, the water flow is controlled, allowing the biozone to form over a period of weeks. The effluent water may be tested at this time to determine the potability of the water and effectiveness of the filter.

Once established and after reaching appropriate maturity, the biologically active layer is removed, and the removed material is evaluated for its biological characteristics, for example the amount and type of any bacteria, fungi, protozoa, rotifer, aquatic insect larvae, or larger aquatic organisms such as bryzoa, snails, or Annelid worms. It is anticipated that the characteristics of the material may be similar due to the use of similar filter setups, or may be different due to the use of biologically non-identical inflowing water sources.

Example 3

Effectiveness of the Inoculant in Slow-Sand Filtration

The inoculant of Example 1 is placed into a clean P3 BioS and Bag Filter, and the filter is filled with sand. The previously harvested filter is left intact and is used as a control to determine the effectiveness of the experimental filter containing the inoculant. Water flow is established over both of the filters, using the non-sterile inflowing water source of Example 1 or the water sources of Example 2.

To determine the amount of time needed for each filter to generate potable water, the biological layers of each bag are monitored, as is the potability of the effluent water, as determined by relevant measures, i.e. particulate load and reduction, bacterial speciation, organic load analysis, nitrogen loads and reduction, or coliform load and reduction. It is anticipated that the experimental filter containing the preserved material will generate potable water more rapidly than the control filter, and/or will generate a more functional biologically active layer over a given amount of time.

Example 4

Creation of Inoculant From Municipal Water Treatment Device

A municipal water treatment device having a functioning biologically active layer is located. The functionality of the biologically active layer is determined by the suitability of the effluent water for one or more uses, and may be determined by testing of the effluent.

Biologically active material is removed from the water treatment device. Removed material is freeze-dried or dehydrated by conventional methods to form the inoculant, and is stored for later use. The remaining sand is left intact in the filter for future regeneration of the biologically active layer.

Example 5

Effectiveness of the Inoculant in a Municipal Water Treatment Device

The inoculant of Example 4 is placed into a separate, newly established or recently cleaned municipal water treatment device, and the device is brought into service. The previously harvested device is left intact and is used as a control to determine the effectiveness of the experimental device containing the inoculant. Water flow is established over both of the devices, using a non-sterile wastewater source such as sewage.

To determine the amount of time needed for each device to generate treated water, the biological layers of each device are monitored, as is usefulness or cleanliness of the effluent water, as determined by relevant measures, i.e. particulate load and reduction, bacterial speciation, organic load analysis, nitrogen loads and reduction, or coliform load and reduction. It is anticipated that the experimental filter containing the preserved material will generate suitably treated water more rapidly than the control filter, and/or will generate a more functional biologically active layer over a given amount of time.

What is claimed is:

1. A method for producing potable water using a sand filter water treatment device, the method comprising:
   (a) removing a first biofilm layer from the sand filter water treatment device;
   (b) obtaining a second biofilm layer grown using a second device that is distinct from the sand filter water treatment device;
   (c) removing water from the second biofilm layer to obtain a preserved inoculant;
   (d) adding one or more nutrients including a sugar to one or more of the second biofilm layer or the preserved inoculant;
   (e) subsequent to removing the first biofilm layer, introducing the preserved inoculant and the one or more nutrients including the sugar to the sand filter water treatment device; and
   (f) filtering a source water supply through the sand filter water treatment device to produce the potable water.

2. The method of claim 1, wherein:
   the second biofilm layer includes organisms comprising at least one of bacteria, fungi, protozoa, rotifera, aquatic insect larvae, or algae;
   the obtaining the second biofilm layer comprises removing the second biofilm layer as a substantially intact biofilm layer; and
   the substantially intact biofilm layer contains substantially all of the organisms found in the second biofilm layer from a top to a bottom of the second biofilm layer.

3. The method of claim 2, wherein the second biofilm layer is grown in the second device by agitating the organisms in a medium comprising the one or more nutrients.

4. The method of claim 2, wherein:
   the first biofilm layer comprises first organisms with regional characteristics of the sand filter water treatment device; and
   the second biofilm layer comprises second organisms with the regional characteristics different from the first organisms.

5. The method of claim 1, wherein:
   prior to removal of the first biofilm layer from the sand filter water treatment device, a flow rate of source water through the first biofilm layer on the sand filter water treatment device is below an effective flow rate;
   a sufficient amount of the first biofilm layer is removed from the sand filter water treatment device to restore the effective flow rate; and
   the preserved inoculant and the one or more nutrients are introduced to the sand filter water treatment device having the effective flow rate.

6. The method of claim 1, wherein the potable water is removed from the second biofilm layer by dehydration or freeze drying.

7. The method of claim 2, wherein the substantially intact biofilm layer is preserved by dehydration.

8. A method for generating an inoculant for water treatment, comprising:
   (a) harvesting biologically active material from a first device;
   (b) filtering the harvested biologically active material through a filter to remove debris;
   (c) dehydrating the filtered harvested biologically active material to form a preserved inoculant;
   (d) adding a sugar to the preserved inoculant to create a seeding material;
   (e) adding the seeding material to a second device having a filtering media that is configured to filter particulates in conjunction with the seeding material; and
   (f) treating water from a source by passing the water through the second device to produce potable water.

9. The method of claim 8, wherein the method further comprises:
   (g) prior to dehydrating the filtered harvested biologically active material, culturing the filtered harvested biologically active material to increase an amount of the biologically active material.

10. The method of claim 9, wherein:
    the culturing of the filtered harvested biologically active material is performed in a laboratory container containing a nutrient-rich growth medium; and
    the nutrient-rich growth medium comprises the sugar and one or more of carbohydrates, vitamins, minerals, or pH modifiers.

11. The method of claim 8, wherein:
    the harvested biologically active material comprises microorganisms;
    the filtering further removes sand; and
    the filtering does not remove the microorganisms.

12. The method of claim 8, wherein the second device is a wastewater treatment device selected from one or more of a biological, aerobic, anaerobic, digestor, lagoon, or reactor-based device.

13. A composition of an inoculant for use in producing potable water, the inoculant comprising:
    a biomaterial harvested from a first device and preserved by removal of water from the biomaterial, the biomaterial comprising microorganisms; and
    one or more nutrients including a sugar that provide food for selective growth of the microorganisms, wherein the inoculant, when introduced to a sand water treatment device, generates a new biologically active layer for use in the sand water treatment device to produce the potable water.

14. The composition of claim 13, wherein:
    the biomaterial is removed as a substantially intact piece from the first device; and
    the biomaterial is formed by dehydrating the substantially intact piece.

15. The composition of claim 14, wherein:
    the dehydration preserves the microorganisms in the inoculant for use in generating the new biologically active layer in the sand water treatment device; and
    the microorganisms comprise bacteria and at least one of fungi, protozoa, rotifera, aquatic insect larvae, or algae.

16. The composition of claim 15, wherein:
    when introduced to the sand water treatment device, the inoculant forms a solution comprising the microorganisms, and the one or more nutrients including the sugar; and
    the one or more nutrients comprise at least one of carbohydrates, vitamins, minerals, or pH modifiers.

17. The composition of claim 13, wherein:
    the microorganisms comprise at least one of bacteria, fungi, protozoa, rotifera, aquatic insect larvae, or algae;
    the biomaterial harvested from the first device comprises a substantially intact piece of the biomaterial; and
    the new biologically active layer contains substantially all of the microorganisms found in the biomaterial from a top to a bottom of the biomaterial.

18. The composition of claim 13, wherein the microorganisms in the inoculant are not directly derived from a biologically active zone of the sand water treatment device.

19. The composition of claim 13, wherein the biomaterial is filtered to remove debris and sand.

\* \* \* \* \*